Figure 1:
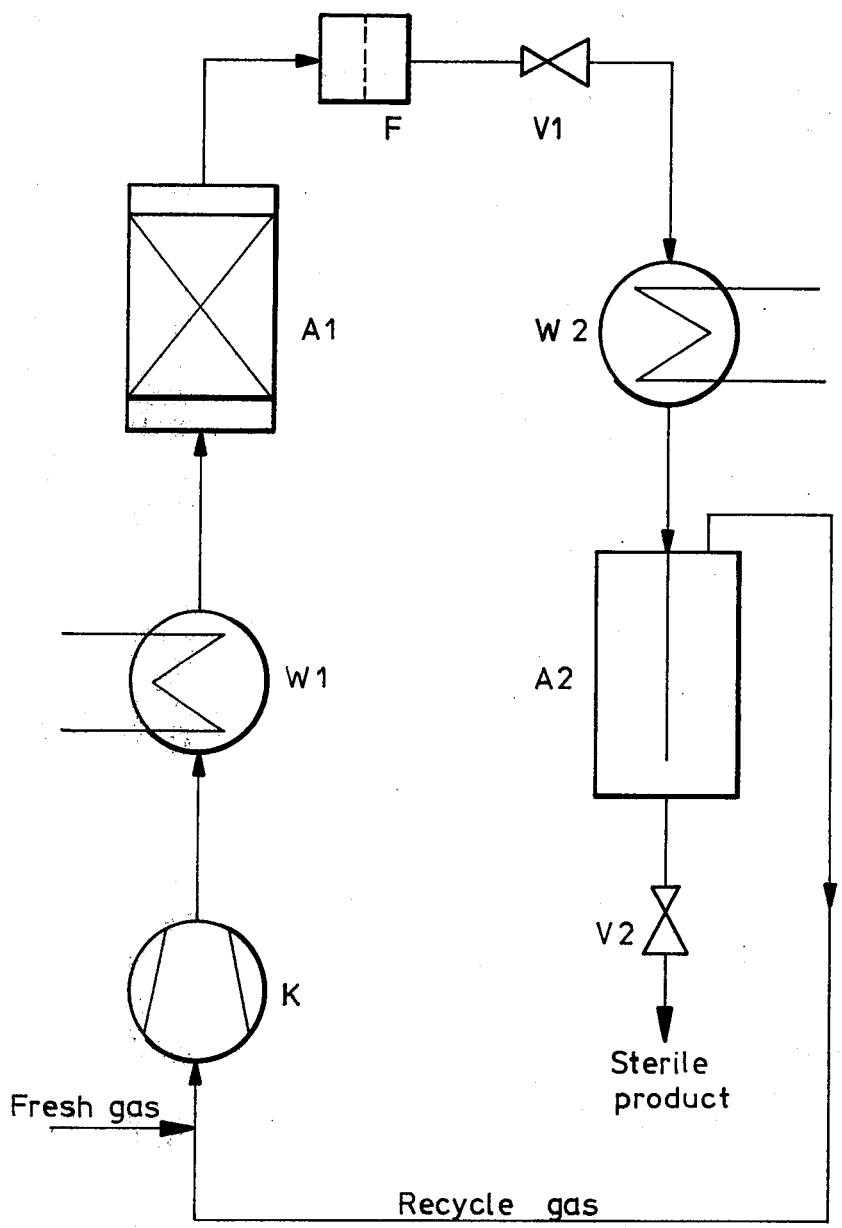

United States Patent [19]
Pilz et al.

[11] 4,263,253
[45] Apr. 21, 1981

[54] PROCESS FOR RENDERING SOLIDS STERILE

[75] Inventors: Volker Pilz, Cologne; Roland Rupp, Leverkusen, both of Fed. Rep. of Germany

[73] Assignee: Bayer Aktiengesellschaft, Leverkusen, Fed. Rep. of Germany

[21] Appl. No.: 62,275

[22] Filed: Jul. 30, 1979

[30] Foreign Application Priority Data

Aug. 25, 1978 [DE] Fed. Rep. of Germany ....... 2837115

[51] Int. Cl.³ .............................................. A61L 2/02
[52] U.S. Cl. .......................................... 422/1; 55/57; 55/82; 422/38; 422/39
[58] Field of Search ................... 422/1, 38, 39; 55/82, 55/57, 279; 210/501

[56] References Cited

U.S. PATENT DOCUMENTS 3,477,856  1/1969  Schultz ................................. 426/424

FOREIGN PATENT DOCUMENTS 2043537  5/1972  Fed. Rep. of Germany .
2127611 12/1972  Fed. Rep. of Germany .
 694001  7/1953  United Kingdom ...................... 422/38
1290117  9/1972  United Kingdom .
1388581  3/1975  United Kingdom .

OTHER PUBLICATIONS

S. J. Hopkins, *Pharmaceutical Aspects of Sterilization*, Feb. 1949, pp. 56–61.

*Primary Examiner*—S. Leon Bashore
*Assistant Examiner*—Michael L. Goldman
*Attorney, Agent, or Firm*—Sprung, Felfe, Horn, Lynch & Kramer

[57] ABSTRACT

The present invention relates to a process for freeing solids, in particular pharmaceutical active ingredients, from germs by sterile filtration using supercritical gases.

6 Claims, 1 Drawing Figure

PROCESS FOR RENDERING SOLIDS STERILE

The present invention relates to a process for freeing solids, in particular pharmaceutical active ingredients, from germs by sterile filtration using supercritical gases.

A series of sterilization processes for the preparation of sterile powders and solids are known at the present time. In the case of heat-stable compounds, heat sterilization, that is to say warming up to 140 to 180° C., is frequently used. At temperatures below 140° C., complete sterilization is frequently not guaranteed. Powder sterilization using antiseptic gases, in particular by gassing with ethylene oxide, can only be carried out industrially with particular precuationary measures because ethylene oxide forms an explosive mixture with air. Furthermore, such gassing processes and likewise heat sterilization do not achieve any further purification effects such as, for example, separation of fibres and other solid foreign particles. In the case of particularly reactive substances, there is also the danger of a chemical reaction with ethylene oxide (compare Galenisches Praktikum (Galenic Practical Course), K. Müzel et al, 822–829, (1959) and Hagers Handbuch der Pharmazeutischen Praxis (Hager's Handbook of Pharmaceutical Practice), 4th. edition, volume 7, part A, 369 (1971)).

Processes for the preparation of sterile powders by freeze-drying sterile-filtered, mostly aqueous solutions of medicaments are also known. These methods are expensive on the industrial scale and can only be used in the case of substances which are soluble in water and resistant to hydrolysis.

The sterile preparation of powders using organic solvents is likewise customary, the dissolved substance being initially sent through a sterile filter and then precipitated from the solvent. A considerable disadvantage of this process lies in the fact that the substances worked up in this way still contain solvent residues and can only be obtained free from solvent by expensive methods.

The disadvantage mentioned in the case of sterile preparation can be avoided by using, instead of liquid organic solvents, other substances, which, on the one hand, are capable of dissolving the substances to be sterilized, but which, on the other hand, are themselves sparingly soluble in these substances, so that a quantitative recovery of the solute is simply and easily possible.

Gases which are known to be capable, in the compressed and particularly in the supercritical condition, of even dissolving substances which are not easily volatilised are suitable for this purpose. When the pressure is lowered, this solvent capacity is very rapidly lost (frequently already in the region from 20 to 50 bars) and the solubility of the gas in the substance which is then precipitated also becomes so small with decreasing pressure that, when the pressure is lowered to atmospheric pressure, previously dissolved substances are recovered in very pure form.

The described solubility effect in compressed supercritical gases, which has moreover already been known for approximately 100 years (see, for example, Hannay and Hogarth, Proc. Roy. Soc. 30 (1880), 178), but which has fallen back into oblivion in the meantime, is currently utilized in the separation of mixtures of substances. Thus, a process for the decaffeination of raw coffee has been described in German Patent Specification No. 2,005,293 and a process for the extraction of nicotine from tobacco has been described in German Patent Specification No. 2,043,537, supercritical gases (for example carbon dioxide) being used. Processes for the preparation of hop extracts and spice extracts, likewise using supercritical gases, are described in German Patent Specification Nos. 2,127,618 and 2,127,611. The solvent capacity of supercritical gases is also employed in high-pressure gas chromatography (see, for example, Chemie-Ingenieur-Technik, volume 42, number 13 (1970), pages 702–704 and 890–898).

The use of supercritical gases for the sterile preparation of solids, in particular of pharmaceutical active ingredients, has hitherto not been disclosed.

As used herein, reference to "supercritical" conditions means under conditions which are above critical temperature and pressure and a "supercritical gas" is a gas under supercritical conditions.

The present invention relates to a process for rendering solids sterile in which a solid is dissolved in a gas or gas mixture which is under supercritical conditions of temperature and pressure, and the resulting solution is then transported through a sterile-filter. Preferably the sterile fluid gas solids mixture is thereafter separated into solid and gas again, downstream of the filter by letting down the pressure and/or varying the temperature.

This sterilization process with supercritical gases is particularly suitable for solids which are required to be very pure, in particular for active ingredients for medicaments. Examples of suitable solids are analgesics such as aspirin and antibiotics such as ampicillin and azlocillin.

The process according to the invention permits a discontinuous or continuous procedure whereby sensitive substances can be kept sterile, without loss and without troublesome solvent impurities, under mild conditions. Possible working gases for the sterile filtration according to the invention are: carbon dioxide, nitrous oxide, lower hydrocarbons (for example ethane, ethylene, propane and propylene), lower halogenhydrocarbons (for example trifluorochloromethane, fluoroform ($CHF_3$) and difluorochloromethane) and also sulphur hexafluoride and ammonia, these being used by themselves or in mixtures with one another and also "doped", that is to say provided with small percentages of medium- and higher-boiling components such as, for example, water, alcohols and higher hydrocarbons.

The process according to the invention is preferably carried out in a temperature range from 20° to 140° C. More preferably it is carried out in a temperature range from 30° to 80° C.

The process is preferably carried out at pressures between 20 and 1,200 bars. More preferably it is carried out at pressures between 50 and 1,000 bars.

A possible industrial embodiment of the process according to the present invention is illustrated schematically with reference to the accompanying drawing (FIG. 1).

The working gas is condensed to the desired operating pressure in a compressor K and, in the downstream heat exchanger W1, it is heated to a temperature which as a rule is only a few degrees above the critical temperature of the gas (or gas mixture). In the apparatus A1, which is a solution vessel in which the product to be freed from germs is placed, the gas is now charged with this product. The fluid mixture which forms is then sent through the sterile filter F where bacteria and germs are retained. By letting the pressure down at the valve V1 and/or changing the temperature in the heat exchanger W2, the sterile homogeneous gas/substance mixture is then separated into two phases, namely the sterile solid phase, which can be taken off as sterile end product from the bottom of the pressure vessel (separator) A2, and a less condensed gas phase which is very extensively freed from solid and is fed back to the compressor as recycle gas.

Further embodiments of this process are characterized in that, after compression, the working gas can be doped with higher-boiling components (water, alcohols or hydrocarbons), in that the dissolving process and in particular the separation process are carried out in several stages which are distinguished by different pressure and/or different temperature, and in that the process is also operated continuously with respect to the product to be sterilised, that is to say it is operated with constant supply and removal of substance.

The process for the production of sterile solids according to the present invention will now be illustrated by the following Examples.

EXAMPLE 1

A fixed amount of acetylsalicyclic acid in the form of a powder charge is placed in a vessel A1 in an apparatus according to FIG. 1. A stream of supercritical carbon dioxide having a temperature of $T=50°$ C. is passed continuously through this charge. The gas speed, relative to the free cross-section, is of the order of magnitude of $w_o = 0.1 \div 1.10^{-3}$ meters/second and the mean contact time between gas and solid is 5 to 30 minutes. At a pressure of 500 bars in the vessel A1 and of 1 to 50 bars in the vessel A2, 1.9 g of sterile product are obtained per cubic meter (S.T.P.) of carbon dioxide pumped round.

EXAMPLE 2

Under conditions identical to those in Example 1, but with a dissolving pressure of $P=900$ bars, the yield is: 4.9 g of sterile product per cubic meter (S.T.P.) of carbon dioxide pumped round.

EXAMPLE 3

In an identical arrangement to that in Example 1, the active ingredient ampicillin sodium is sterilized with $N_2O$ at 40° C. and 100 bars. 0.1 g of sterile active ingredient is obtained per cubic meter (S.T.P.) of $N_2O$.

EXAMPLE 4

Under conditions identical to those in Example 3, 0.15 g of sterile substance is obtained per cubic meter (S.T.P.) of $N_2O$ from the active ingredient azlocillin sodium.

EXAMPLE 5

Using Freon 13, doped with 2% of Freon 11, in the arrangement according to Example 1, 70 mg of the active ingredient azlocillin sodium are obtained per cubic meter (S.T.P.) of gas mixture at 100 bars and 30° C.

What is claimed is:

1. A process for rendering solids sterile, which comprises dissolving a solid in a single gas or mixture of gases under supercritical conditions, with respect to pressure and temperature, of the single gas or mixture of gases, and transporting the resulting solution through a sterile filter to provide a sterile fluid gas/solid mixture.

2. A process according to claim 1, in which the process is carried out in a temperature range from 20 to 140° C. and in a pressure range from 20 to 1,200 bars.

3. A process according to claim 2, in which the temperature range is from 30° to 80° C. and the pressure range is from 50 to 1,000 bars.

4. A process according to claim 1, 2 or 3 in which the solid is a pharmaceutically active ingredient.

5. A process according to claim 1 in which the sterile fluid gas/solid mixture is separated into solid and gas again, downstream from the filter, by letting down the pressure and/or varying the temperature.

6. A process according to claim 1 in which all or part of the gas is recirculated.

* * * * *